United States Patent [19]

Kraska

[11] 4,211,794

[45] Jul. 8, 1980

[54] N,N-DISUBSTITUTED AMINOMETHYLPHENYLETHANOLA-MINES

[75] Inventor: Allen R. Kraska, East Lyme, Conn.

[73] Assignee: Pfizer Inc., New York, N.Y.

[21] Appl. No.: 1,989

[22] Filed: Jan. 8, 1979

[51] Int. Cl.$^2$ .................. A61K 31/135; C07C 91/16; C07C 91/22
[52] U.S. Cl. .................................. 424/330; 260/570.6
[58] Field of Search ...................... 424/330; 260/570.6

[56] References Cited

U.S. PATENT DOCUMENTS

| | | | |
|---|---|---|---|
| 3,872,171 | 3/1975 | Cronin et al. | 424/250 |
| 4,034,040 | 7/1977 | Cronin et al. | 424/330 |

FOREIGN PATENT DOCUMENTS

| | | | |
|---|---|---|---|
| 50-5342 | 1/1975 | Japan | 260/570.6 |
| 50-36434 | 4/1975 | Japan | 260/570.6 |

OTHER PUBLICATIONS

Sill et al., J. Med. Chem., 17, p. 965 (1974).

*Primary Examiner*—Allen J. Robinson
*Attorney, Agent, or Firm*—F. X. Murphy; C. J. Knuth; A. J. Nelson

[57] ABSTRACT

The novel N,N-bis(higher-n-alkyl)aminomethylphenylethanolamines and their mineral acid and organic acid salts are useful for preventing viral infections in mammals and also for stimulating cellular mediated immune response.

11 Claims, No Drawings

N,N-DISUBSTITUTED AMINOMETHYLPHENYLETHANOLAMINES

BACKGROUND OF THE INVENTION

Virus infections which attack mammals, including man, are normally contagious afflictions which are capable of causing great human suffering and economic loss. Unfortunately, the discovery of antiviral compounds is far more complicated and difficult than the discovery of antibacterial and antifungal agents. This is due in part, to the close structural similarity of viruses and the structure of certain essential cellular components such as ribonucleic and deoxyribonucleic acids. Nevertheless, numerous non-viral "antiviral agents", i.e. substances "which can produce either a protective or therapeutic effect to the clear detectable advantage of the virus infected host, or any material that can significantly enhance antibody formation, improve antibody activity, improve non-specific resistance, speed convalescence or depress symptoms" [Herrman et al., Proc. Soc. Exptl. Biol. Med., 103, 625 (1960)], have been described in the literature. The list of reported antiviral agents includes, to name a few, interferon and synthetic materials such as amantadine hydrochloride, pyrimidines, biguanides, guanidine, pteridines and methisazone. Because of the rather narrow range of viral infections that can be treated by each of the antiviral agents commercially available at the present time, new synthetic antiviral agents are always welcomed as potentially valuable additions to medical technology.

The cells of mammals produce, in response to virus infection, a substance which enables cells to resist the multiplication of a variety of viruses. The viral-resisting or viral-interfering substances are referred to as "interferons". The interferons are glycoproteins which may differ in their physico-chemical properties, but all exhibit the same biological properties; namely they inhibit a wide range of unrelated viruses, have no toxic or other deleterious effects on cells, and are species-specific (Lockart, Frontiers of Biology, Vol. 2, "Interferons", edited by Finter, W. B. Saunders Co., Philadelphia, 1966, pages 19-20).

No practical, economical method has yet been developed for the preparation of exogenous interferon for routine clinical use against viral infections. An alternative approach to producing interferon has, therefore, been pursued, which comprises administering a non-viral substance which stimulates or induces production of interferon in the cells. The interferon produced in this fashion is referred to as "endogenous" interferon.

Several types of polyamines are known to stimulate interferon production and hence have antiviral activity. They include the polyamines disclosed in U.S. Pat. No. 3,872,171, the xylenediamines disclosed in U.S. Pat. No. 4,034,040, and the phenethanolamine substituted, glycerin-based lipids disclosed in Ser. No. 825,535 allowed Feb. 12, 1979, now U.S. Pat. No. 4,166,132. Other related phenthanolamine substituted, glycerin-based lipids not having antiviral activity are disclosed in Ser. No. 906,260 allowed Feb. 12, 1979, now U.S. Pat. No. 4,173,641.

SUMMARY OF THE INVENTION

According to the invention, an N,N-disubstituted aminomethylphenylethanolamine or its pharmacologically acceptable mineral acid or organic acid salt is capable of combatting viral infections in mammals by stimulating or inducing the production of endogenous interferon. The structural formula of the aminomethylphenylethanolamine is:

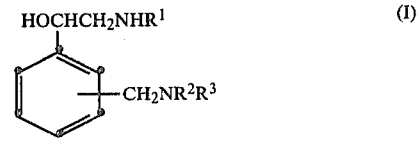

wherein $R^1$ is hydrogen or alkyl having from 1 to 4 carbon atoms, $R^2$ and $R^3$ are the same or different and each is n-alkyl of from 12 to 20 carbon atoms and the benzene ring is meta or para-disubstituted.

A preferred embodiment of the invention is the aminomethylphenylethanolamine wherein $R^2$ and $R^3$ are the same. This type of amine group substitution facilitates synthesis as a result of the commercial availability of the corresponding starting material amine, $R^2R^3NH$. Other preferred embodiments of the invention are the two aminomethylphenylethanolamines wherein $R^2$ and $R^3$ are each n-tetradecyl and wherein $R^2$ and $R^3$ are each n-hexadecyl. These substitutions tend to optimize the anti-viral activity.

Especially preferred embodiments of the invention include the aminomethylphenylethanolamine wherein $R^1$ is hydrogen, the benzene ring is meta-disubstituted and $R^2$ and $R^3$ are each n-hexadecyl; the aminomethylphenylethanolamine wherein $R^1$ is ethyl, the benzene ring is meta-disubstituted and $R^2$ and $R^3$ are each n-hexadecyl; the aminomethylphenylethanolamine wherein $R^1$ is isopropyl, the benzene ring is meta-disubstituted and $R^2$ and $R^3$ are each n-hexadecyl; and the aminomethylphenylethanolamine wherein $R^1$ is t-butyl, the benzene ring is meta-disubstituted and $R^2$ and $R^3$ are each n-hexadecyl. Their biological activities in the antiviral and other tests described infra make them outstanding examples of the present invention.

The invention also includes a pharmaceutical formulation of an N,N-disubstituted aminomethylphenylethanolamine of the invention or its pharmacologically acceptable salt and methods of treating a viral infection and inducing the production of interferon using such an aminomethylphenylethanolamine or salt. The pharmaceutical formulation is useful for the treatment of an interferon sensitive viral infection in a mammal and comprises an antivirally effective amount of an aminomethylphenylethanolamine or its salt and a pharmaceutically acceptable carrier. The method of prophylactically controlling an interferon sensitive viral infection in a mammal comprises administering to the host an antivirally effective amount of an aminomethylphenylethanolamine or its salt and the method of inducing the production of interferon in a mammal comprises administering an effective amount of an aminomethylphenylethanolamine or its salt.

DETAILED DESCRIPTION OF THE INVENTION

In accordance with the invention an aminomethylphenylethanolamine of formula I is prepared, as illustrated in Scheme A, infra, by an amination reaction of an epoxide of formula II using an amine of formula $R^1NH_2$.

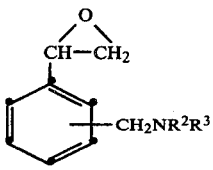

In general, the amination reaction procedure follows methods well known in the art and any may be employed with success. In usual practice, the reaction may be conducted neat, in an excess of $R^1NH_2$ at a temperature range of from about 30° to 130° under sealed vessel conditions until the reaction is substantially complete. As a common alternative, the reaction may be conducted in a polar, protic or aprotic solvent at a temperature from about 30° to reflux until the reaction is substantially complete. Useful polar solvents include dimethylformamide, dimethylacetamide, dimethylsulfoxide, dioxane, chloroform, methanol, ethanol and the like. When using a polar, protic solvent it is advantageous to use an excess of the amine $R^1NH_2$. Under any procedure, a stoichiometric ratio of epoxide to amine should be used and an excess of the amine will usually provide a favorable yield.

Workup and isolation of the aminomethylphenylethanolamine can be accomplished in any manner known to those in the art. In general, chromatographic, extraction, distillation and recrystallization techniques can be used with success. In usual practice, excess solvent and amine may be removed using ordinary techniques, followed by chromatography of the aminomethylphenylethanolamine. Alternatively, or in addition, the aminomethylphenylethanolamine may be dissolved in a suitable solvent, converted to its hydrochloride salt and recrystallized using ordinary techniques.

Preparation of the epoxide of formula II, in turn, follows methods well known in the art. The synthetic sequence is illustrated by reactions (1), (2) and (3) of Scheme A infra and may be described as follows.

Reaction (1): An alpha halo meta or para tolunitrile of formula III is reacted with a disubstituted amine of formula $HNR^2R^3$ is polar, aprotic solvent while optionally using a suitable hydrogen halide neutralizing agent, to form an N,N-disubstituted aminomethylbenzonitrile of formula IV.

Reaction (20: The benzonitrile of formula IV is then partially reduced and hydrolyzed to form an N,N-disubstituted aminomethylbenzaldehyde of formula V. Appropriate reducing agents include hydrogen and nickel catalyst using hydrazine followed by aqueous sulfuric acid; nickel-aluminum amalgam, formic acid and water; lithium triethoxyaluminum hydride; sodium triethoxyaluminum hydride; stannous chloride and hydrogen chloride followed by water; and diisobutylaluminum hydride. A preferred reducing agent is diisobutyl aluminum hydride. Use of these reducing agents is well known in the art. Reduction by any of these methods will produce in situ the intermediate Schiff base which is then hydrolyzed to the benzaldehyde of formula V by water present in the reaction mixture or by addition of water to the reaction after reduction is complete.

Reaction (3): The epoxide of formula II is prepared from the benzaldehyde of formula V by reaction with the sulfur ylide, dimethyloxosulfonium methylide, or other appropriate sulfur ylide in a suitable solvent such as ether, tetrahydrofuran, glyme, diglyme, dioxane and the like. This method is well-known in the art.

The three steps described constitute the preparatory method for the epoxide of formula II and together with the amination reaction described supra constitute the entire synthesis of an aminomethylphenylethanolamine of formula I as given by Scheme A.

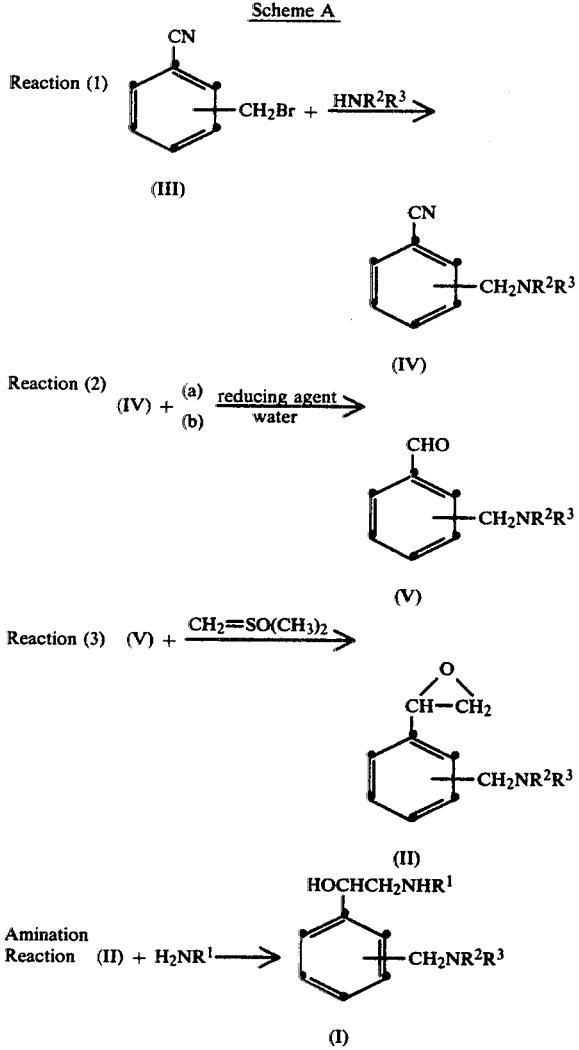

It will be appreciated that the N,N-disubstituted aminomethylphenylethanolamines of the invention may also be synthesized using other routes and techniques that are thoroughly familiar to those skilled in the art.

Pharmacologically acceptable mineral acid or organic acid salts of the aminomethylphenylethanolamines of this invention may be formed by methods known to those familiar with the art. Suitable mineral acids appropriate for the salt formation include, but are not limited to, hydrochloric, hydrobromic, hydroiodic, sulfuric and phosphoric acid and the like. Suitable organic acids appropriate for salt formation include, but are not limited to, tartaric, citric, glycolic, propionic, butyric, succinic, maleic, gluconic, lauric, malonic, fumaric, stearic, lactic, palmoic, isobutyric, benzoic, and tosic acids and the like.

The novel aminomethylphenylethanolamines of this invention and the pharmacologically acceptable salts thereof are effective in treating viral infections by stimulating or inducing the production of endogenous interferon and in stimulating cellular mediated immune response. Examples 5, 6 and 7 illustrate the achievement of these effects and are standard biological tests to determine (a) prophylatic ability to protect against encephalomycarditis (EMC) virus, (b) ability to promote rejection of Sarcoma 180J tumor cells and (c) ability to non-specifically stimulate peritoneal macrophages.

The novel aminomethylphenylethanolamines of this invention can be used in a variety of pharmaceutical formulations which contain the compound or a pharmacologically acceptable salt thereof, and may be administered by a variety of conventional routes, such as intravenous, intramuscular, subcutaneous, intranasal, topical and intraperitoneal.

The aminomethylphenylethanolamines or their pharmacologically acceptable salts may be administered alone or in combination as a pharmaceutical formulation using pharmaceutically acceptable carrier material such as inert solid diluents, aqueous solutions or various non-toxic, organic solvents in dosage forms such as gelatin capsules, tablets, powders, lozenges, syrups, injectable solutions and the like. Such formulation material may include water, ethanol, gelatins, lactose, starches, vegetable oils, petroleum jelly, gums, glycols, talc, benzyl alcohols and other known carriers for medicaments. If desired, these pharmaceutical formulations may also contain auxillary material such as preserving agents, wetting agents, stabilizing agents, lubricating agents, absorption agents, buffering agents and isotonic agents and the like.

Although the particular dose, formulation and route of administration are dependent upon each patient's unique condition and the wisdom of his attending physician, the guidelines set forth infra for the aminomethylphenylethanolamines of this invention and the pharmacologically acceptable salts thereof describe their usefulness as antiviral agents and as agents for non-specific stimulation of cell mediated immunity.

Generally, when used as an antiviral agent through the mediation of induced, endogenous interon, administration before exposure to an infectious virus will provide rapid resistance to the virus. Preferably, administration should take place from about two days to about one day before exposure to the virus, although this will vary somewhat with the particular patient and the particular infectious virus.

For prophylactic use against viral infection, the aminomethylphenylethanolamines of this invention may be administered by any of the routes mentioned supra in the appropriate pharmaceutical formulation containing a dose of about 1 mg./kg. to about 250 mg./kg. of aminomethylphenylethanolamine with about 1 to 4 doses per day being employed. The preferred range of the dose of aminomethylphenylethanolamine to be used is about 5 mg./kg. to about 50 mg./kg. Administration of a pharmacologically acceptable salt of the invention will follow the same procedure with a corresponding adjustment of the dose given.

Generally, when used to stimulate cell mediated immunity, suitable pharmaceutical formulations containing small doses of the aminomethylphenylethanolamines of this invention will be administered initially and may be increased gradually to determine the optimum dosage for the particular patient. His or her immune competence will generally be monitored following administration, using conventional techniques employed in the art, such as the macrophage activation assay described hereinafter. Typically, maximum activation will be observed about 24 to 48 hours after the initial administration and, absent administration of further doses, will decline to the initial level over a further 24 to 48 hour period. Thus, administration of a second dose approximately 24 to 72 hours after the initial administration will maintain the desired level of immune competence. Generally, 2 to 4 doses will be administered in this manner and the response to treatment of the patient determined. Further doses may then be administered if necessary, as described above. Administration of a pharmacologically acceptable salt of the invention will follow the same procedure.

The present invention is illustrated by the following examples. It should be understood, however, that the invention is not limited to the specific details of these examples. All temperatures are in degrees centigrade and if not specified, are ambient temperature.

EXAMPLE 1

Preparation of
N-ethyl-2-[meta-N,N-di-n-hexadecylaminomethylphenyl]ethanolamine (1-I)

The following procedure gives the entire synthetic sequence used to prepare the title compound (1-I) as a hydrochloride salt and follows the sequence outlined in Scheme A supra.

3-(N,N-Di-n-hexadecylaminomethyl)benzonitrile
(1-IV)

α-Bromo-m-tolunitrile (1-III) (3.9 g, 0.02 mol), di-n-hexadecylamine (9.3 g, 0.02 mol), and potassium carbonate (27.6 g 0.2mol) were combined in dimethylacetamide (93 ml) and heated (80°–90°; 1.5 hr). The mixture was then poured over ice, stirred cold (15 min), and filtered. The resulting solids were washed with water, dissolved in hexane (70 ml), and filtered. The hexane solution of product was dried over sodium sulfate, filtered and concentrated to an oil under reduced pressure. The oil was dissolved in isopropyl alcohol, cooled in an ice water bath, and the resulting crystals isolated and dried to give benzonitrile 1-IV (7.2 g, 62% yield): mp 26°–27°; ir (CHCl$_3$) 2225 cm$^{-1}$.

3-(N,N-Di-N-hexadecylaminomethyl)benzaldehyde
(1-V)

3-(N,N-Di-n-hexadecyl-aminomethyl)benzonitrile (1-IV) (40 g, 0.069 mole) was dissolved in hexane (300 ml) and treated with 0.807 M diisobutylaluminum hydride (60 ml, 0.048 mol) at room temperature under a nitrogen atmosphere. The resulting solution was stirred (4 hr) and then worked up by adding methanol (25 ml) and water (15 ml). This mixture was then filtered and concentrated under reduced pressure to give an oil, which was further purified by silica gel column chromatography (eluted with a benzene/ethanol gradient mixture) to give the pure aldehyde (1-V): oil; ir (neat) 1690 cm$^{-1}$.

N,N-Di-n-hexadecyl-3-(1,2-epoxyethyl)benzylamine
(1-II)

Sodium hydride (12.12 g of a 57% dispersion in mineral oil, 0.288 mol) was added to dimethylsulfoxide (350 ml) and the mixture heated (70°–80° C.) under a nitrogen atmosphere for 45 min. The resulting solution was then diluted with tetrahydrofuran (350 ml), cooled to 0°–5° C., and treated with portions of trimethylsulfonium iodide (50.8 g, 0.288 mol) over a 5 min period. 3-(N,N-Di-n-hexadecylaminomethyl)-benzaldehyde (1-V) (48 g, 0.0872 mol) dissolved in tetrahydrofuran (100 ml) was then added rapidly and the reaction mixture was allowed to stir for 16 hr. The resulting mixture was poured into water (800 ml) and extracted with ether (3×250 ml). The combined ether extracts were washed with water (3×350 ml) and saturated sodium chloride solution (350 ml), dried over magnesium sulfate, filtered, and concentrated under reduced pressure to give the desired epoxide (1-II): oil (51 g, 98% yield); NMR (CDCl$_3$) δ 2.82 (d of d, 1H), 3.17 (d of d, 1H), 3.90 (d of d, 1H).

N-ethyl-2-(meta-N,N-di-n-hexadecylaminomethylphenyl)-ethanolamine (1-I) as a hydrochloride salt.

A mixture of N,N-di-n-hexadecyl-3-(1,2-epoxyethyl)-benzylamine (1-II) (3.7 g, 0.0062 mol) and ethylamine (27.6 g, 0.61 mol) was placed in a steel bomb and heated at 90° C. for 8 hr (75 psi). The reaction mixture was then concentrated under reduced pressure and the resulting oil purified by silica gel chromatography (eluted with a benzene/ethanol gradient mixture). The desired amine 1-I was converted to the hydrochloride salt by passing hydrogen chloride through a solution of it in ethyl acetate followed by recrystallization from the same solvent (0.4 g, 10% yield): mp 89°–90° C. (HCl salt); NMR (CDCl$_3$) δ 1.48 (t, 3H).

|  | C | H | N |
|---|---|---|---|
| Analysis calc'd for C$_{43}$H$_{82}$N$_2$O . 2HCl | 72.21 | 11.85 | 3.92 |
| Found | 71.79 | 11.84 | 3.92 |

EXAMPLE 2

N-t-butyl-2-[meta-N,N-di-n-hexadecylamino-methylphenyl]ethanolamine (2-I)

Following the procedure of Example 1 and substituting t-butyl amine for ethyl amine in the amination reaction converting (1-II) to (1-I), the title compound (2-I) as a hydrochloride salt was prepared. m.p. 114°–116° (HCl salt).

|  | C | H | N |
|---|---|---|---|
| Analysis Calc'd for C$_{45}$H$_{86}$N$_2$O . 2HCl | 72.64 | 11.92 | 3.76 |
| Found | 72.35 | 11.64 | 3.60 |

EXAMPLE 3

N-isopropyl-2-[meta-N,N-di-n-hexadecylaminomethylphenyl]ethanolamine (3-I)

Following the procedure of Example 1 and substituting isopropyl amine for ethylamine in the amination reaction converting (1-II) to (1-I), the title compound (3-I) as a hydrochloride salt was prepared. m.p. 107°–109° (HCL salt).

|  | C | H | N |
|---|---|---|---|
| Analysis calc'd for C$_{44}$H$_{84}$N$_2$O . 2HCl | 72.39 | 11.87 | 3.84 |
| Found | 72.15 | 11.69 | 3.60 |

EXAMPLE 4

2-[meta-N,N-di-n-hexadecylaminomethylphenyl]ethanolamine (4-I)

Following the procedure of Example 1, epoxide (1-II) was prepared. It was used in the procedure infra to prepare the title compound (4-I) as a hydrochloride salt.

A solution of N,N-di-n-hexadecyl-3-(1,2-epoxyethyl)-benzylamine (1-II) (3.3 g, 5.5 mmol) and sodium azide (1.5 g, 23 mmole) in 80 ml of dioxane was stirred, heated to reflux for about 16 hrs. The solvent was then removed in vacuo and the resulting crude residue purified by silica gel chromatography (eluted with benzene/ethanol gradient mixture). The desired intermediate azide was isolated (1.5 g oil) and was reduced with lithium aluminum hydride (0.71 g.) in ether to give the desired amine. It was converted to the hydrochloride salt by passing hydrogen chloride through a solution of it and ethyl acetate following by recrystallization from the same solvent to yield the title compound (4-I) as a hydrochloride salt (0.5 g) (mp 90°–92°).

|  | C | H | N |
|---|---|---|---|
| Analysis calc'd for C$_{91}$H$_{78}$N$_2$O . 2HCl | 71.58 | 11.72 | 4.07 |
|  | 71.48 | 11.75 | 3.92 |

Examples 1–4 demonstrate that the other N,N-disubstituted aminomethylphenylethanolamines of the invention can be prepared by substituting the appropriate amine HNR$^2$R$^3$ for di-n-hexadecylamine of the Example 1 conversion step (1-III) to (1-IV) and by substituting the appropriate amine R$^1$NH$_2$ for ethyl amine of the Example 1 conversion step (1-II) to (1-I) or by forming the primary amine according to the procedure of Example 4.

EXAMPLE 5

Prophylactic use of compounds (1-I), (2-I) and (3-I) against infection by encephalomyocardis viral infection in mice Three groups of ten female albino micce (20–25 g. body weight) were given single 0.5 ml. intraperitoneal injections containing dosage levels of 1.5, 5, and 15 mg. of the appropriate compound/kg. body weight, respectively. A fourth control group was given no such injection. Eighteen to twenty-four hours later all four groups were challenged with a 0.2 ml. subcutaneous injection containing 20–30 times the LD$_{50}$, the dosage level causing a 50% death rate in ten days, of encephalomyocarditis (EMC) virus. The following relative average survival rates were found from an average of 2 such runs for compounds 1-I, 2-I and 3-I.

|  | Average Relative Survival (Sr) | |
|---|---|---|
| Compound | Dose (mg/kg) | Sr |
| 1-I | 15 | 70 |
| 1-I | 5 | 65.5 |
| 1-I | 1.5 | 24.5 |
| 2-I | 15 | 65.5 |
| 2-I | 5 | 62.5 |
| 2-I | 1.5 | 42.5 |
| 3-I | 15 | 87.5 |
| 3-I | 5 | 54 |
| 3-I | 1.5 | 27 |

Antiviral activity is expressed as the average relative survival (Sr) of 2 runs of experimental groups compared to the controls on the tenth day after challenge. Sr is defined by the formula $$S_r = S_x + \frac{\sum_{i=1\ to\ 10} x_i - \sum_{i=1\ to\ 10} e_i}{100 + 100 - \sum_{i=1\ to\ 10} e_i} \times 100$$

wherein
Sr = relative survival;
$S_x$ = percent survival after ten days in experimental group;
$X_i$ = number of survivors on the ith day in experimental group;
$e_i$ = number of survivors on the ith day in control group.

EXAMPLE 6

Sarcoma 180J Model for Assessment of Tumor Rejection

Six female CD-1 mice (20–25 g) per group received $10^6$ S-180J cells (5–8 days old) intraperitoneally (i.p.) on day O. The animals then received formulated drug (0.1 ml) at the desired dose on day 1 following tumor cell injection. The animals were observed until death or 40 days, whichever occurred first. Results using compounds 1-I, 2-I, 3I and 4I are expressed as percent life span (% ILS).

$$\% \ ILS = \frac{Mean\ Survival\ Drug\ Treated}{Mean\ Survival\ Controls} \times 100$$

| Compound | %ILS[b] | | 50 (Dose in mg./kg.) |
|---|---|---|---|
|  | 5 | 15 |  |
| 1-I[a] | 150(1) | 210(4) | 235(5) |
| 2-I | 154(1) | 134 | 160(2) |
| 3-I | 154(2) | 185(4) | 212(6) |
| 4-I | 125 | 181(4) | 212(6) |

[a]compounds were formulated in TWEEN 80/glycerol aqueous suspensions.
[b]Numbers in parenthesis are numbers of 40 day survivors.

EXAMPLE 7

Peritoneal Exudate Cell Mediated Cytotoxicity in Vitro

Peritoneal exudate cells (PEC) from normal mice injected with immune potentiators or drug vehicle were harvested by gentle lavage with 3 ml cold RPMI 1640 medium (Grand Island Biological Co., N.Y.) supplemented with 5 units of heparin per ml of medium. Macrophages were identified morphologically, counted, and adjusted to $7.5 \times 10^5$ cells per ml of tissue culture medium; 0.2 ml volumes were added to microtiter wells containing $10^4$ B-16 cells with $^{125}$IUDR label (effector: target cell ratio = 15:1). After 24 hours at 37° in 5% $CO_2$, supernatants were decanted and the adherent cells washed 3 times with pre-warmed RPMI 1640; the supernatant and washings were pooled and retained for counting. The adherent cells were treated with 1% sodium dodecyl sulfate (SDS) at room temperature for 30 minutes. The SDS-treated cells were harvested and the cells washed 3 times with RPMI 1640; cells and washings were pooled for counting. Supernatants and cells were counted in a Searle 1185 gamma counter. Results were expressed as:

$$Percent\ ^{125}IUDR\ release = \frac{cpm\ supernatant}{cpm\ cells + cpm\ supernatant} \times 100$$

The table below gives the percent cytotoxicity for 1-I, 2-I and 3-I wherein Percent Cytotoxicity equals (Percent release from drug-treated) minus (Percent release from vehicle treated).

| Compound | % Cytotoxicity | | |
|---|---|---|---|
|  | 1 | 5 | 25 (Dose in mg/kg) |
| 1-I | 35.7 | 25.6 | 23.8 |
| 2-I | 31.2 | 33.6 | 27.2 |
| 3-I | 42.4 | 35.1 | 33.4 |

I claim:
1. An N,N-disubstituted aminomethylphenylethanolamine of the formula

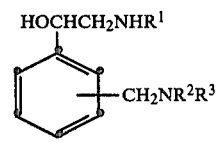

or its pharmacologically acceptable mineral acid or organic acid salt wherein:
$R^1$ is hydrogen or alkyl having 1 to 4 carbon atoms;
$R^2$ and $R^3$ are the same or different, each being normal alkyl of from 12 to 20 carbon atoms; and
the benzene ring is meta or para disubstituted.

2. An aminomethylphenylethanolamine of claim 1 wherein $R^2$ and $R^3$ are the same.

3. An aminomethylphenylethanolamine of claim 1 wherein $R^2$ and $R^3$ are each n-tetradecyl.

4. An aminomethylphenylethanolamine of claim 1 wherein $R^2$ and $R^3$ are each n-hexadecyl.

5. The aminomethylphenylethanolamine of claim 4 wherein $R^1$ is hydrogen and the benzene ring is meta disubstituted.

6. The aminomethylphenylethanolamine of claim 4 wherein $R^1$ is ethyl and the benzene ring is meta disubstituted.

7. The aminomethylphenylethanolamine of claim 4 wherein $R^1$ is isopropyl and the benzene ring is meta disubstituted.

8. The aminomethylphenylethanolamine of claim 4 wherein $R^1$ is t-butyl and the benzene ring is meta disubstituted.

9. A pharmaceutical formulation useful for the treatment of interferon sensitive viral infection in a mammal, which comprises an antivirally effective amount of an aminomethylphenylethanolamine of claim 1 and a pharmaceutically acceptable carrier.

10. A method of prophylactically controlling an interferon sensitive viral infection in a mammal, which comprises administering to the mammal an antivirally effective amount of an aminomethylphenylethanolamine of claim 1.

11. A method of inducing the production of interferon in a mammal, which comprises: administering to said mammal an amount effective to induce the production of interferon of a compound of claim 1.

* * * * *